United States Patent
Bakeman et al.

(10) Patent No.: US 10,012,606 B1
(45) Date of Patent: Jul. 3, 2018

(54) X-RAY BASED METROLOGY WITH PRIMARY AND SECONDARY ILLUMINATION SOURCES

(71) Applicant: KLA-Tencor Corporation, Milpitas, CA (US)

(72) Inventors: Michael S. Bakeman, Fremont, CA (US); Xuena Zhang, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/748,108

(22) Filed: Jun. 23, 2015

Related U.S. Application Data

(60) Provisional application No. 62/016,487, filed on Jun. 24, 2014.

(51) Int. Cl.
    *G01N 23/227*   (2018.01)
    *G01N 23/223*   (2006.01)
    *G01N 23/2273*  (2018.01)
    *G01N 23/207*   (2018.01)

(52) U.S. Cl.
    CPC ..... *G01N 23/2273* (2013.01); *G01N 23/2076* (2013.01); *G01N 23/223* (2013.01)

(58) Field of Classification Search
    None
    See application file for complete search history.

(56) References Cited

U.S. PATENT DOCUMENTS

| | | | |
|---|---|---|---|
| 3,919,548 A * | 11/1975 | Porter | G01N 23/2204 313/467 |
| 5,315,113 A * | 5/1994 | Larson | G01N 23/227 250/305 |
| 5,497,008 A * | 3/1996 | Kumakhov | B82Y 10/00 250/505.1 |
| 5,608,526 A | 3/1997 | Piwonka-Corle et al. | |
| 5,859,424 A | 1/1999 | Norton et al. | |
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |

(Continued)

*Primary Examiner* — Wyatt Stoffa
*Assistant Examiner* — James Choi
(74) *Attorney, Agent, or Firm* — Spano Law Group; Joseph S. Spano

(57) ABSTRACT

Methods and systems for performing relatively high energy X-ray Fluorescence (XRF) measurements and relatively low energy X-ray photoelectron spectroscopy (XPS) measurements over a desired inspection area of a specimen are presented. Combined XPS and XRF measurements of a specimen are achieved with illumination tailored to each respective metrology technique. A high brightness, high energy x-ray illumination source is employed in combination with one or more secondary fluorescence targets. The high energy x-ray illumination source supplies high energy x-ray illumination to a specimen to perform high energy XRF measurements. In addition, the high energy x-ray illumination source supplies high energy x-ray illumination to one or more secondary fluorescence targets. The one or more secondary fluorescence targets absorb some of the high energy x-ray photons and emit x-ray emission lines at a lower energy. The relatively low energy x-ray illumination is directed to the specimen to perform relatively low energy XPS measurements.

18 Claims, 4 Drawing Sheets

(56) References Cited

U.S. PATENT DOCUMENTS

| | | | |
|---|---|---|---|
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 7,478,019 B2 | 1/2009 | Zangooie et al. | |
| 7,826,071 B2 | 11/2010 | Shchegrov et al. | |
| 7,929,667 B1 * | 4/2011 | Zhuang | H05G 2/005 378/119 |
| 7,933,026 B2 | 4/2011 | Opsal et al. | |
| 2003/0149189 A1 * | 8/2003 | Cheung | C08F 212/00 525/332.9 |
| 2004/0247080 A1 * | 12/2004 | Feda | G01N 23/223 378/101 |
| 2006/0120508 A1 * | 6/2006 | Chen | G01N 23/02 378/84 |
| 2006/0167651 A1 * | 7/2006 | Zangooie | G01B 11/0625 702/179 |
| 2009/0268877 A1 * | 10/2009 | Schueler | G01N 23/2273 378/207 |
| 2013/0077742 A1 | 3/2013 | Schueler et al. | |
| 2013/0304424 A1 * | 11/2013 | Bakeman | G03F 7/70625 702/189 |
| 2014/0019097 A1 | 1/2014 | Bakeman et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2017/0176357 A1 * | 6/2017 | Pois | G01N 23/2206 |

\* cited by examiner

X-RAY BASED METROLOGY WITH PRIMARY AND SECONDARY ILLUMINATION SOURCES

CROSS REFERENCE TO RELATED APPLICATION

The present application for patent claims priority under 35 U.S.C. § 119 from U.S. provisional patent application Ser. No. 62/016,487, entitled "Metrology Apparatus with XPS, XRF, and Secondary Target Capabilities," filed Jun. 24, 2014, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of optical metrology based techniques including scatterometry and reflectometry implementations and associated analysis algorithms are commonly used to characterize critical dimensions, film thicknesses, composition and other parameters of nanoscale structures.

Traditionally, scatterometry measurements are performed on targets consisting of thin films and/or repeated periodic structures. During device fabrication, these films and periodic structures typically represent the actual device geometry and material structure, or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. In addition, the increasing number of parameters required to characterize complex structures (e.g., FinFETs), leads to increasing parameter correlation. As a result, the parameters characterizing the target often cannot be reliably decoupled with available measurements. In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical tools have been developed. For example, tools with multiple angles of illumination, shorter and broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

One of the industry responses to these recent challenges has been to incorporate x-ray metrology techniques such as x-ray photoelectron spectroscopy (XPS) and x-ray fluorescence (XRF). U.S. Patent Publication No. 2013/0077742 by Schueler et al. describes film thickness or dose measurements performed based on a combination of XPS and low energy XRF (LE-XRF). An x-ray illumination source provides x-ray illumination to the specimen and both XPS LE-XRF measurement signals are collected. This ensures that the XPS signal and the LE-XRF signal are both emitted from the same area of the sample under measurement.

The LE-XRF measurements described by Schueler et al. are limited by the low energy of the x-ray source that is required to maintain sufficient XPS photoelectron emission cross section (i.e., XPS signal). Low energy excitation limits the number of elemental lines which can be excited and most of the lines which are excited have significantly weaker fluorescence yield. This limits the effectiveness of LE-XRF measurements.

In one example, Schueler et al. describes an x-ray source that emits Aluminum K$\alpha$ radiation having an energy level of 1.486 keV. Although this energy level is described as suitable for XPS, it has significant disadvantages for XRF. In this example, only fluorescence lines close to 1.486 keV or lower can be excited. For many materials of interest, the majority of fluorescence lines stimulated by this relatively low energy level are either L shell lines or M shell lines. FIG. 1 depicts a plot 10 of fluorescence yield as a function of atomic number. Fluorescence yield is defined as the probability that a core hole in a shell is filled by a radiative process, in competition with nonradiative processes. As illustrated in FIG. 1, the fluorescence yield is much lower for M shell and L shell lines then it is for K shell lines. In practice, the resulting XRF signal intensity of M shell and L shell line emission is orders of magnitude lower than K shell line emission. As a result, LE-XRF signals are typically orders of magnitude lower than high energy XRF signals. Moreover, as illustrated in FIG. 1, low fluorescence yield is especially problematic for low atomic number elements.

In another example, Schueler et al. describes an x-ray source having energy below the absorption edge (k-edge) of silicon (approximately 1.840 keV) as a compromise to obtain useable XPS and LE-XRF signals from the same x-ray source.

Future metrology applications present challenges for metrology due to increasingly small resolution requirements, multi-parameter correlation, increasingly complex geometric structures, and increasing use of opaque materials. Thus, methods and systems for improved measurements are desired.

SUMMARY

Methods and systems for supplying both high energy x-ray illumination to a specimen for XRF measurements and relatively low energy x-ray illumination to the same specimen for XPS measurements are described herein. In this manner, combined XPS and XRF measurements of a specimen are achieved with illumination tailored to each respective metrology technique.

In one aspect, a high brightness x-ray illumination system includes a high energy x-ray illumination source in combination with one or more secondary fluorescence targets. The high energy x-ray illumination source supplies high energy x-ray illumination to a specimen to perform high energy XRF measurements. The use of a high brightness, high energy x-ray source enables high throughput XRF measurements having a high signal to noise ratio. The high energy x-ray illumination stimulates K shell emission and increased fluorescence yield compared to the use of a low energy x-ray source.

In addition, the high brightness x-ray illumination source supplies high energy x-ray illumination to one or more secondary fluorescence targets. The one or more secondary fluorescence targets absorb some of the high energy x-ray photons and emit x-ray emission lines at a lower energy. The relatively low energy x-ray illumination is directed to the specimen to perform relatively low energy XPS measurements. The relatively low energy x-ray radiation allows for high throughput XPS measurements due to the increased photoionization cross section available at lower energies.

In another further aspect, the secondary x-ray targets placed in the path of x-ray beam are interchangeable to deliver tunable radiation to the specimen under XPS measurement.

In another further aspect, the combined metrology tool is operable to control the positioning, angle of incidence, and spot size of the incident XRF illumination beam and the incident XPS illumination beam at the desired inspection area of the specimen at any point in time.

In another aspect, the precision and accuracy of parameters measured with combined XPS and XRF techniques is improved by identifying shared model parameters that can be mathematically resolved using data sets derived from XPS and XRF measurements either sequentially or in parallel. Measuring shared parameters with a diversity of measurement technologies reduces correlations among parameters and improves measurement accuracy.

In yet another aspect, XRF and XPS measurements are performed on a planar specimen (e.g., semiconductor wafer) oriented at a number of different out of plane orientations increases the precision and accuracy of measured parameters. Measuring a location of the specimen at a number of different angles results in an enhanced data set corresponding to that location. Measuring parameters with a deeper, more diverse data set also reduces correlations among parameters and improves measurement accuracy.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
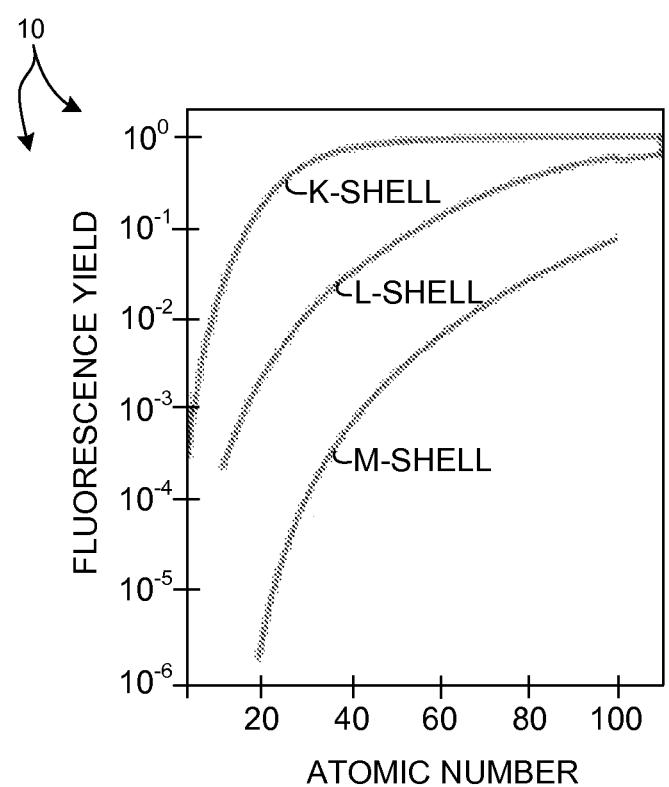
FIG. 1 is a diagram 10 illustrative of fluorescence yield as function of atomic number.

Reference will now be made in detail to background examples and some embodiments of the invention, examples of which are illustrated in the accompanying drawings.

Methods and systems for supplying both high energy x-ray illumination to a specimen for XRF measurements and relatively low energy x-ray illumination to the same specimen for XPS measurements are described herein. In this manner, combined XPS and XRF measurements of a specimen are achieved with illumination tailored to each respective metrology technique.

X-ray radiation penetrates optically opaque thin films, buried structures, high-aspect ratio structures and devices containing many thin film layers that are typically inaccessible by optical radiation. XPS is capable of measuring thin film thickness, and composition, of many different structures and materials near the surface of the specimen under measurement. XRF is also capable of measuring film thickness, and composition, of many different structures and materials at increased depths from the surface of the specimen under measurement.

In one aspect, a high brightness x-ray illumination system includes a high energy x-ray illumination source operating in combination with one or more secondary fluorescence targets. The high energy x-ray illumination source supplies high energy x-ray illumination to a specimen to perform high energy XRF measurements. The use of a high brightness, high energy x-ray source enables high throughput XRF measurements having a high signal to noise ratio. The high energy x-ray illumination stimulates K shell emission and increased fluorescence yield compared to the use of a low energy x-ray source. In some embodiments, the high energy x-ray illumination has an energy level greater than 2 keV. By way of non-limiting example, the high energy x-ray illumination may be provided by emission from copper, molybdenum, indium, or tungsten.

In addition, the high brightness x-ray illumination source supplies high energy x-ray illumination to one or more secondary fluorescence targets. The one or more secondary fluorescence targets absorb some of the high energy x-ray photons and emit x-ray emission lines at a lower energy. In some embodiments, the energy components of the relatively low energy x-ray illumination are less than the absorption edge of Silicon (i.e., less than 1.84 keV). The relatively low energy x-ray illumination is directed to the specimen to perform relatively low energy XPS measurements. The relatively low energy x-ray radiation allows for high throughput XPS measurements due to the increased photoionization cross section available at lower energies. For example, Beryllium and Carbon are elements with a relatively small atomic number with x-ray emission lines that are favorable for XPS measurements. However, electron bombardment of these elements does not result in a sufficiently high brightness x-ray source due to limitations on electron beam power loading. However, since the secondary target is excited by x-ray photon absorption rather than electron beam bombardment, thermal heating of the secondary target is reduced compared to electron beam excitation.

In addition, x-ray excitation of the secondary target results in characteristic line emission from the secondary target without bremsstrahlung emission. In some examples, this significantly reduces the signal to noise of the XPS measurement. In one example, Aluminum may be employed as a secondary target to supply x-ray illumination for XPS measurements without bremsstrahlung emission.

Figure 2:
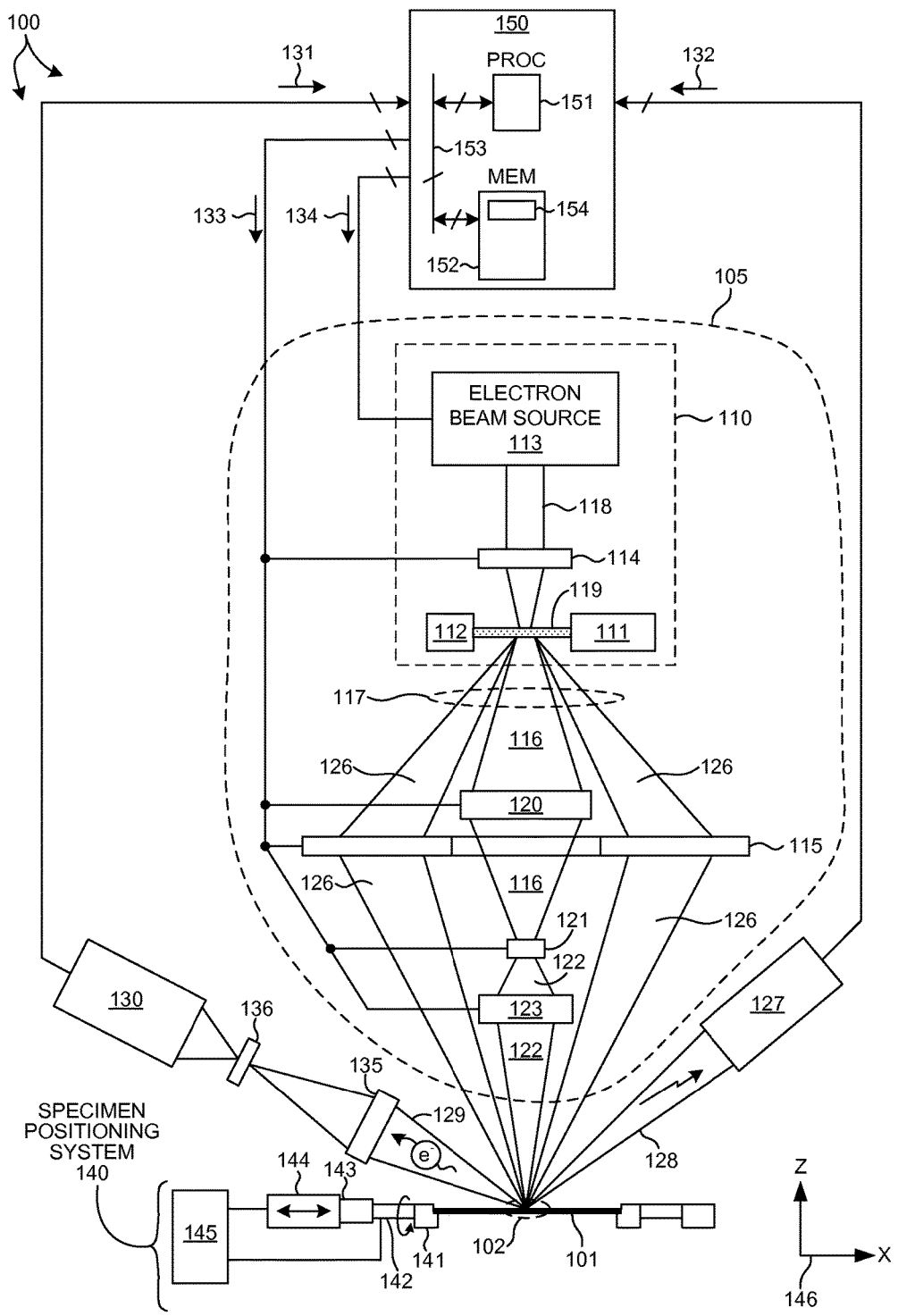
FIG. 2 is a diagram illustrative of an embodiment of a combined metrology system 100 configured to supply x-ray radiation at both low and high energy levels for combined XPS and XRF metrologies.

FIG. 2 illustrates an embodiment of a combined metrology tool 100 for measuring characteristics of a specimen in accordance with the exemplary methods presented herein. As shown in FIG. 2, the system 100 may be used to perform XRF measurements and XPS measurements over an inspection area 102 of a specimen 101 disposed on a specimen positioning system 140.

In the depicted embodiment, metrology tool 100 includes an x-ray illumination system 105 configured to generate x-ray emission lines suitable for combined XRF and XPS measurements. In some embodiments, the x-ray illumination system 105 is configured to generate x-ray emission lines having energy between 100 eV and 80 keV including emission lines less than 1.84 keV at sufficient flux to perform high throughput XPS measurements and emission lines greater than 2.0 keV at sufficient flux to perform high throughput XRF measurements. High throughput measurements include measurements that can be performed with integration times on the order of minutes or less (e.g., less than 10 minutes).

X-ray illumination system 105 includes a primary x-ray illumination source 110 configured to generate high brightness x-rays at flux levels sufficient to enable high-throughput, inline XRF and XPS measurements.

Exemplary x-ray sources include electron beam sources configured to bombard solid or liquid targets to stimulate x-ray radiation. Methods and systems for generating high brightness, liquid metal x-ray illumination are described in U.S. Pat. No. 7,929,667, issued on Apr. 19, 2011, to KLA-Tencor Corp., the entirety of which is incorporated herein by reference. In another example, an inverse Compton source available from Lyncean Technologies, Inc., Palo Alto, Calif. (USA) may be contemplated.

Liquid metal jet x-ray sources replace the solid metal anode with a liquid metal anode, typically an alloy with low melting temperature such as Gallium, Indium and Tin. Since the anode is already a liquid, the electron beam power loading density can be increased much more than is possible with a solid anode. The brightness of an x-ray source (for a given anode material) scales linearly with electron beam power loading density, and consequently liquid anode x-ray sources are much brighter than solid anode sources.

In the embodiment depicted in FIG. 2, primary x-ray illumination source 110 is a liquid metal based x-ray illumination system. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. In one embodiment, the jet of liquid metal includes a Gallium and Indium alloy. In some embodiments, the primary x-ray illumination source 110 is configured to generate x-ray emission lines greater than 2 keV. In some embodiments, the primary x-ray illumination source 110 is configured to generate x-ray illumination having emission lines greater than 8 keV. Exemplary methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces x-ray radiation 117.

In one example, high brightness liquid metal jet x-ray source 110 utilizes an Indium anode. Indium line emission energy is 24.2 keV and is well suited for XRF measurements. The energy level is high enough to excite the K shell lines of more than half of the periodic table. As described hereinbefore with reference to FIG. 1, the fluorescence yield of K shell lines is orders of magnitude greater than the yield of L and M shell lines. Hence, the resulting XRF signals are orders of magnitude greater and the integration time needed to acquire a useable XRF signal is greatly reduced.

While the high energy level of Indium emission is beneficial for XRF measurements, it is detrimental for XPS measurements. To perform an XPS measurement an x-ray photon must be absorbed by the material of interest and stimulate a photoelectron that is ejected from an atom of the material. The photoionization cross section is a measure of the probability that an x-ray of a given energy will be absorbed and produce a photoelectron.

Figure 3:
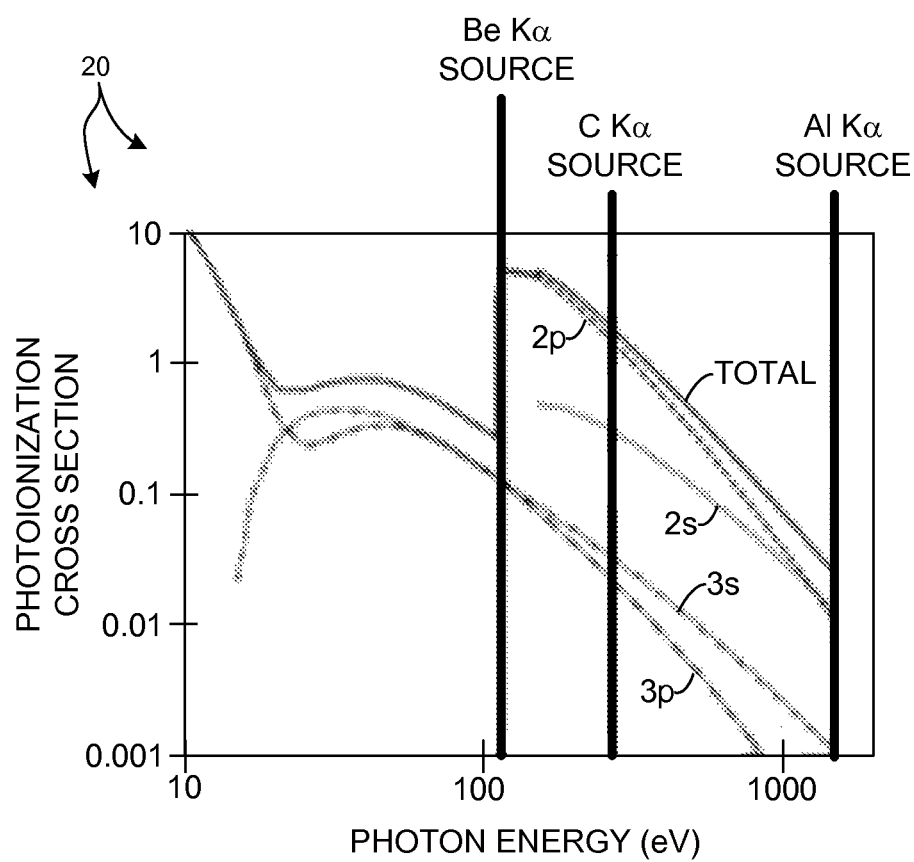
FIG. 3 is a diagram 20 illustrative of the photoionization cross sections of various atomic subshells of Silicon.

FIG. 3 illustrates a plot 20 of the photoionization cross section of Silicon in units of Megabarns/atom. As depicted in FIG. 2, the photoionization cross sections of various atomic subshells of Silicon (e.g., 2p, 2s, 3p, and 3s) all have peaks in the low energy regime (e.g., 10 eV to a few hundred eV) and decay exponentially with increasing x-ray photon energy. For example, an x-ray source emitting low energy x-rays having emission lines around 100-300 eV (e.g., a Beryllium Kα or a Carbon Kα source) produce a much stronger photoelectric response than a higher energy x-ray source (e.g., an Aluminum Kα x-ray source). Hence, an x-ray source emitting low energy x-rays produces a much stronger XPS signal than a higher energy x-ray source such as Aluminum, Copper, or Indium.

In the embodiment depicted in FIG. 2, the primary x-ray illumination source 110 is used to provide high energy x-ray illumination 126 directly to a specimen for XRF measurements. As depicted in FIG. 2, a portion of the x-ray emission 117 is directed toward specimen 101 by x-ray optics 115. In addition, primary x-ray illumination source 110 supplies high energy x-ray illumination 116 to one or more secondary fluorescence targets 121. In response, the one or more secondary fluorescence targets 121 absorb some of the high energy x-ray photons and emit x-ray emission lines at a lower energy. The relatively low energy x-ray illumination 122 is directed to the specimen to perform relatively low energy XPS measurements. The relatively low energy x-ray radiation allows for high throughput XPS measurements due to the increased photoionization cross section available at lower energies. In this manner, x-ray illumination system 105 employs a high energy, primary x-ray illumination source 110 in combination with one or more secondary fluorescence targets 121 to provide relatively low energy x-ray illumination 122 to the specimen for XPS measurements.

In another further aspect, the secondary x-ray targets 121 placed in the path of x-ray beam 116 are interchangeable to deliver tunable radiation to the specimen under XPS measurement.

In some embodiments, x-ray collection optics 115 are oriented in such a way as to optimize x-ray brightness by collecting x-ray radiation over a range of collection angles, $\alpha$. In some examples, $\alpha$, is less than twenty degrees. In some other examples, $\alpha$, is less than ten degrees. In some embodiments, x-ray optics 115 are designed to directly focus radiation of the strongest x-ray line emissions to specimen 101.

In some embodiments, x-ray optics 120 are designed to focus radiation of the strongest x-ray line emissions onto secondary target 121. The secondary target 121 produces x-ray lines of the constituent elements of the secondary target (e.g., Beryllium, Carbon, etc.). The emission from secondary target 121 is subsequently focused onto specimen 101 by x-ray optics 123. In this manner, the x-ray energy produced by x-ray source 110 is reduced before reaching the measurement target to enable high throughput XPS measurements. In addition, this approach reduces the level of background broadband radiation.

X-ray optics 115 shape and direct incident x-ray beam 126 to specimen 101. In some examples, x-ray optics 115 monochromatize the x-ray beam that is incident on the specimen 101. In some examples, x-ray optics 115 collimate or focus the x-ray beam 126 onto inspection area 102 of specimen 101. In some embodiments, x-ray optics 115 includes one or more x-ray collimating mirrors, multilayer mirrors, polycapillary optics, mono-capillary optics, zone plate optics, x-ray apertures, x-ray monochromators, and x-ray beam stops, or any combination thereof.

X-rays 128 are collected by x-ray detector 127 while specimen positioning system 140 locates and orients specimen 101. The x-ray detector 127 is able to resolve one or more x-ray photon energies and produces signals for each x-ray energy component indicative of properties of the specimen. In some embodiments, the x-ray detector 127 includes any of a CCD array, a microchannel plate, a photodiode array, a microstrip proportional counter, a gas filled proportional counter, and a scintillator.

X-ray detector 127 collects x-ray radiation 128 fluoresced from specimen 101 and generates an output signal 132 indicative of properties of specimen 101 that are sensitive to the incident x-ray radiation in accordance with a XRF measurement modality. By way of non-limiting example, the XRF measurement system illustrated in FIG. 2 includes an energy dispersive XRF detector suitable for performing measurements in accordance with an energy dispersive XRF measurement modality. However, in some other embodiments the XRF measurement system includes a wavelength dispersive XRF detector suitable for performing measurements in accordance with a wavelength dispersive XRF measurement modality.

In yet another example, the XRF measurement system illustrated in FIG. 2 is configured as a Total Reflection XRF (TXRF) measurement system. In these embodiments, the incident angle of the XRF illumination beam is below the critical angle for the substrate. In some examples an angle of incidence of approximately 0.05 degrees is employed. TXRF limits the excitation of the sample to the outermost surface and can be used to measure surface metal contamination on wafers, or conformal layers, such as a conformal layer of Germanium over a FinFET structure. TXRF can be used to perform on-device measurements, and is not limited to the small spot (e.g., approximately 50 micrometers, or less) typically required for metrology targets. Due to the larger permissible spot size, a larger incident x-ray flux may be directed to the surface of the specimen under measurement. The resulting reduction in measurement time is desirable, particularly when a wavelength dispersive detector is employed.

In yet another example, the XRF measurement system illustrated in FIG. 2 is configured as a confocal XRF measurement system. In these embodiments, illumination optics such as illumination optics 115 are configured to collimate the incident x-ray radiation over a small volume of the specimen 101 under inspection. Similarly, collection optics (not shown) are employed to collect fluoresced radiation from the illuminated volume and project the collected radiation onto detector 127. In some embodiments, the illumination and collection optics are polycapillary optics. In confocal XRF, the field of view of the illumination and collection optics is relatively small (e.g., less than 100 $um^3$, or approximately 10 $um^3$ in some cases) compared to conventional XRF measurements. In this manner, spatially resolved, localized thin film and composition measurements can be performed using confocal XRF with a high degree of precision.

X-ray optics 120 shape and direct incident x-ray beam 116 to secondary target 121. In some examples, x-ray optics 120 monochromatize the x-ray beam that is incident on secondary target 121. In some examples, x-ray optics 120 collimate or focus the x-ray beam 116 onto secondary target 121. In some embodiments, x-ray optics 120 includes one or more x-ray collimating mirrors, x-ray apertures, x-ray monochromators, and x-ray beam stops, or any combination thereof.

X-ray optics 123 shape and direct low energy x-ray beam 122 from secondary target 121 to specimen 101. In some examples, x-ray optics 123 monochromatize the x-ray beam 122 that is incident on the specimen 101. In some examples, x-ray optics 123 collimate or focus the x-ray beam 122 onto inspection area 102 of specimen 101. In some embodiments, x-ray optics 123 includes one or more x-ray collimating mirrors, x-ray apertures, x-ray monochromators, and x-ray beam stops, or any combination thereof.

Photoelectrons 129 are collected by electron collection optics 135 and focused onto analyzer 136. In one example, analyzer 136 is a hemispherical analyzer that includes a magnetic and electrostatic field along a single axis. This disperses the electrons with respect to energy along one axis, and does not disperse the electrons with respect to energy along the other axis. The resulting field of electrons is detected by detector 130 while specimen positioning system 140 locates and orients specimen 101. By way of non-limiting example, detector 130 may be a solid state detector, a microchannel plate, or a phosphor coupled to a charge coupled device (CCD). In some examples detector 130 is a two dimensional detector employed in conjunction with a hemispherical analyzer as described hereinbefore. In these embodiments, detector 130 is able to resolve one or more electron energies along one axis and produce signals for each electron energy component indicative of properties of the specimen. In addition, the two dimensional detector is able to resolve the spatial distribution of the collected electron field along the other axis. The resulting spatial distribution is also indicative of properties of the specimen.

In this manner, detector 130 collects photoelectrons 129 emitted from specimen 101 and generates an output signal 131 indicative of properties of specimen 101 that are sensitive to the incident photoelectrons in accordance with a XPS measurement modality.

Combined metrology tool 100 also includes a computing system 150 employed to acquire signals 132 and 131 generated by XRF detector 127 and photoelectron detector 130, respectively, and determine properties of the specimen based at least in part on the acquired signals. As illustrated in FIG. 2, computing system 150 is communicatively coupled to XRF detector 127 and photoelectron detector 130.

In a further embodiment, computing system 150 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In some embodiments, the primary x-ray illumination source (e.g., primary x-ray illumination source 110) is a single source that generates x-ray illumination, directly or indirectly, for both XRF and XPS measurements. However, in some other embodiments, multiple x-ray sources are combined to generate x-ray illumination, directly or indirectly, for both XRF and XPS measurements.

In a further aspect, secondary x-ray targets can be placed in the path of x-ray beam 126, causing the secondary targets to fluoresce. The secondary fluorescence can then be used to excite the specimen for XRF measurements. This is useful for two purposes. First, an x-ray source employing an electron beam such as a rotating anode or a liquid metal jet illumination source will generate bremsstrahlung radiation. Bremsstrahlung radiation arises from the interaction of the electron beam with the primary target. This background radiation shows up as noise in measurements of samples illuminated, in part, by this radiation. To minimize bremsstrahlung radiation, a secondary target is introduced into the XRF illumination sub-system. The primary radiation generated by the interaction of the electron beam with the primary target is used to excite the secondary target. The emission from the secondary target does not include bremsstrahlung radiation because the secondary target is excited by photons rather than electrons. The emission from the secondary target is then used to illuminate the sample, rather than the emission from the primary target. This increases the signal to noise of the XRF measurement. Secondly, since the radiation from a secondary target is emitted at the characteristic energy levels of the secondary target, a change in material composition of the secondary target can be used to change the x-ray energy incident upon the sample. This is useful to increase the x-ray absorption of elements whose absorption edges are far from the primary target energies. Again, this is useful for increasing the signal to noise of an XRF measurement. Thus, in some embodiments, the XRF illumination sub-system includes multiple interchangeable secondary target materials to deliver tunable radiation to the specimen under measurement. Materials suitable as secondary targets include any material having a longer x-ray wavelength compared to the primary target.

In a preferred embodiment, specimen 101, electron collection optics 135, analyzer 136, photoelectron detector 130, and x-ray detector 127 are maintained in a vacuum environment suitable for efficient transmission of electrons. However, in some embodiments, the x-ray detector 127 is maintained in a separate environment (e.g., atmospheric) from the vacuum environment. In these embodiments, the x-ray detector is separated from the vacuum environment by a vacuum window. The vacuum window may be constructed of any suitable material that is substantially transparent to x-ray radiation (e.g., Beryllium). In these embodiments, scattered x-ray radiation 128 passes through the vacuum window and is incident on an x-ray detector 127 that is contained in a separate environment.

In some embodiments, the incident XRF illumination beam 126 and the incident XPS illumination beam 122 spatially overlap at the inspection area 102 of the specimen 101. Furthermore, in some embodiments, the incident XRF illumination beam 126 and the incident XPS illumination beam 122 spatially overlap at the inspection area 102 of the specimen 101 at the same time. Thus, in one aspect, computing system 150 receives measurement data 131 and 132 associated with simultaneous measurements of specimen 101 over an inspection area 102 illuminated by both an x-ray illumination beam 126 configured for XRF measurements and an x-ray beam 122 configured for XPS measurements.

In another further aspect, combined metrology tool 100 includes a computing system (e.g., computing system 150) configured to implement beam control functionality as described herein. In the embodiment depicted in FIG. 2, computing system 150 is configured as a beam controller operable to control the positioning, angle of incidence, and spot size of the incident XRF illumination beam 126 and the incident XPS illumination beam 122 at the desired inspection area 102 of the specimen 101 at any point in time. In addition, computing system 150 is configured as a beam controller operable to control the control the illumination properties of the incident XRF illumination beam 126 and the incident XPS illumination beam 122 such as spot size, spectral purity, divergence, intensity, polarization, and spectrum of the respective x-ray beams.

As illustrated in FIG. 2, computing system 150 is communicatively coupled to XPS detector 130 and XRF detector 127. Computing system 150 is configured to receive measurement data 132 from XRF detector 127 and measurement data 131 from XPS detector 130. In one example, measurement data 132 includes an indication of the measured XRF response of the specimen. Based on the distribution of the measured XRF response on the surface of detector 127, the location and area of incidence of XRF illumination beam 126 on specimen 101 is determined by beam controller 150. In one example, pattern recognition techniques are applied by computing system 150 to determine the location and area of incidence of XRF illumination beam 126 on specimen 101 based on measurement data 132. Similarly, measurement data 131 includes an indication of the measured XPS response of the specimen. Based on the distribution of the measured XPS response on the surface of detector 130, the location and area of incidence of XPS illumination beam 122 on specimen 101 is determined by beam controller 150. In one example, pattern recognition techniques are applied by computing system 150 to determine the location and area of incidence of XPS illumination beam 122 on specimen 101 based on measurement data 131. In response computing system 150 generates command signals 133 to electron beam source 113 and command signals 134 communicated to any of illumination optics 114, 120, 115, 123, and a targeting positioning system of target 121 to redirect and reshape incident XRF illumination beam 126 and incident XPS illumination beam 122 such that the desired beam properties, location, and angle of incidence are achieved.

In another aspect, XPS and XRF measurements of a particular inspection area are performed at a number of different out of plane orientations. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy.

As illustrated in FIG. 2, combined metrology tool 100 includes a specimen positioning system 140 configured to both align specimen 101 and orient specimen 101 over a large range of out of plane angular orientations with respect the XRF and the XPS detectors. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by metrology system 100 over any number of locations on the surface of specimen 101. In one example, computing system 150 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 2, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 2. As depicted in FIG. 2, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

Each of the XPS and XRF measurement modules described hereinbefore is capable of performing stand-alone measurements and analysis. In some examples, XPS and XRF measurements are performed sequentially or simultaneously to characterize the same or different material or structural properties of a specimen based on decoupled XPS and XRF analyses.

However, in yet another aspect, the precision and accuracy of parameters measured with either or both XPS and XRF techniques can be improved by identifying shared model parameters that are mathematically resolved using data sets derived from XPS and XRF measurements either sequentially or in parallel. Measuring shared parameters with a diversity of measurement technologies reduces correlations among parameters and improves measurement accuracy.

The combined fitting of XRF metrology data and XPS metrology data is advantageous for any type of XPS and XRF technology that provides complementary sensitivity to geometric and/or material parameters of interest. This is specifically the case where at least one geometric (e.g., film thickness) or material parameter is common between the XPS and the XRF models. Specimen parameters can be deterministic (e.g., film thicknesses, composition, stoichiometry, CD, SWA, grating height, etc.) as long as proper models describing XPS and XRF beam interaction with the specimen are used.

Measurement accuracy may be enhanced by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

The combined use of high energy XRF and relatively low energy XPS enables measurement of structures and materials at a variety of depths. High flux, high energy x-ray radiation penetrates into opaque areas of the target that enables characterization of buried structures, high aspect ratio structures, and devices including many thin film layers. Examples of characteristics measured using combined XRF and XPS as described herein include but are not limited to film thickness, elemental composition, and stoichiometry.

Examples of structures measured using combined XRF and XPS as described herein include but are not limited to photoresist and other patterning materials in double-patterning or multiple-patterning processes, FinFETs, low-dimensional structures such as nanowires or graphene, sub 10 nm structures, thin films, lithographic structures, through substrate vias (TSVs), memory structures such as DRAM, DRAM 4F2, FLASH and high aspect ratio memory structures. In some examples, combined XRF and XPS enable the measurement of features smaller than 10 nm as well as advanced semiconductor structures such as spin-transfertorque MRAM where measurements of geometrical parameters and material parameters are needed.

The combined use of high energy XRF and relatively low energy XPS enables measurement of in-die targets, actual device targets, or proxy targets having larger dimensions.

It should be recognized that the various steps described throughout the present disclosure may be carried out by a single computer system 150 or, alternatively, a multiple computer system 150. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 150 may be configured to perform any other step(s) of any of the method embodiments described herein.

In addition, the computer system 150 may be communicatively coupled to the XRF detector 127, the XPS detector 130, any of the illumination optics, the specimen positioning system 140, and a secondary target positioning system in any manner known in the art. For example, the one or more computing systems 150 may be coupled to computing systems associated with the XRF detector 127, the XPS detector 130, any of the illumination optics, the specimen positioning system 140, and the secondary target positioning system, respectively.

The computer system 150 of the combined metrology system 100 may be configured to receive and/or acquire data or information from the subsystems of the system (e.g., XRF detector 127, XPS detector 130, any of the illumination optics, the specimen positioning system 140, the secondary target positioning system, and the like) by a transmission medium that may include wireline and/or wireless portions. In this manner, the transmission medium may serve as a data link between the computer system 150 and other subsystems of the system 100.

Computer system 150 of the combined metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 150 and other systems (e.g., memory on-board metrology system 100, external memory, or external systems). For example, the computing system 150 may be configured to receive measurement data (e.g., signals 130 and 131) from a storage medium (i.e., memory 152) via a data link. For instance, spectral results obtained using a spectrometer of any of XPS detector 130 and XRF detector 127 may be stored in a permanent or semi-permanent memory device (e.g., memory 152). In this regard, the spectral results may be imported from on-board memory or from an external memory system. Moreover, the computer system 150 may send data to other systems via a transmission medium. For instance, specimen parameter values determined by computer system 150 may be stored in a permanent or semi-permanent memory device (e.g., memory 152). In this regard, measurement results may be exported to another system.

Computing system 150 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 154 implementing methods such as those described herein may be transmitted over a transmission medium such as a wire, cable, or wireless transmission link. For example, as illustrated in FIG. 2, program instructions stored in memory 152 are transmitted to processor 151 over bus 153. Program instructions 154 are stored in a computer readable medium (e.g., memory 152). Exemplary computer-readable media include read-only memory, a random access memory, a magnetic or optical disk, or a magnetic tape.

In some embodiments, a combined XPS and XRF analysis as described herein is implemented as part of a fabrication process tool. Examples of fabrication process tools include, but are not limited to, lithographic exposure tools, film deposition tools, implant tools, and etch tools. In this manner, the results of a combined XPS and XRF analysis are used to control a fabrication process. In one example, XPS and XRF measurement data collected from one or more targets is sent to a fabrication process tool. The XPS and XRF measurement data is analyzed as described herein and the results used to adjust the operation of the fabrication process tool.

Figure 4:
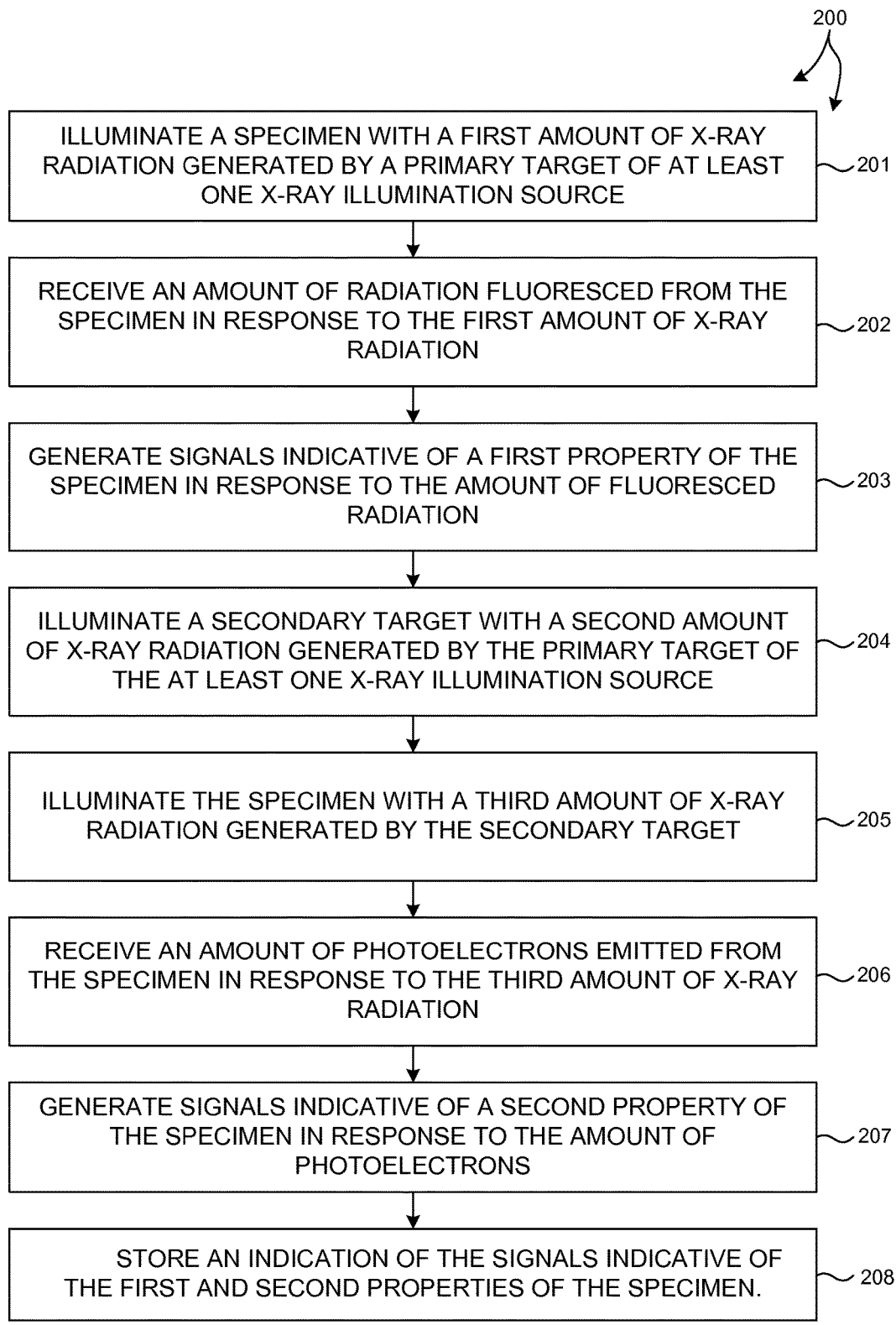
FIG. 4 is a flowchart illustrative of method 200 suitable for implementation by the combined metrology system 100 of the present invention.

FIG. 4 illustrates a method 200 suitable for implementation by the combined metrology system 100 of the present invention. In one aspect, it is recognized that data processing blocks of method 200 may be carried out via a pre-programmed algorithm executed by one or more processors of computing system 150. While the following description is presented in the context of combined metrology system 100, it is recognized herein that the particular structural aspects of combined metrology system 100 do not represent limitations and should be interpreted as illustrative only.

In block 201, a specimen is illuminated by an first amount of x-ray radiation generated by a primary target of at least one x-ray illumination source.

In block 202, an amount of radiation flouresced from the specimen in response to the first amount of x-ray radiation is received.

In block 203, signals indicative of a first property of the specimen are generated in response to the amount of flouresced radiation.

In block 204, a secondary target is illuminated with a second amount of x-ray radiation generated by the primary target of the at least one x-ray illumination source.

In block 205, the specimen is illuminated with a third amount of x-ray radiation generated by the secondary target.

In block 206, an amount of photoelectrons emitted from the specimen is received in response to the third amount of x-ray radiation.

In block 207, signals indicative of a second property of the specimen are generated in response to the amount of photoelectrons.

In block 208, an indication of the signals indicative of the first and second properties of the specimen are stored in a memory (e.g., memory 152).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology tool comprising:
an x-ray illumination source configured to generate a first amount of x-ray radiation directed to a specimen;
a secondary fluorescence target configured to absorb a second amount of x-ray radiation from the x-ray illumination source, and, in response to the absorbed amount of x-ray radiation, emit a third amount of x-ray radiation directed to the specimen, the third amount of x-ray radiation having a lower energy than the second amount of x-ray radiation;
a x-ray detector configured to receive an amount of radiation scattered from the specimen in response to the first amount of x-ray radiation and generate signals indicative of a first property of the specimen, wherein the x-ray illumination source and the x-ray detector are disposed in a X-Ray Fluorescence (XRF) measurement configuration;
a photoelectron detector configured to receive an amount of electrons emitted from the specimen in response to the third amount of x-ray radiation and generate signals indicative of a second property of the specimen, wherein the x-ray illumination source, the secondary target, and the photoelectron detector are disposed in a X-Ray Photoelectron Spectroscopy (XPS) measurement configuration; and
a beam controller operable to communicate a command signal to an x-ray illumination optics subsystem that changes a position of incidence of the first amount of x-ray radiation on the specimen under measurement in response to the command signal, wherein the command signal is determined based at least in part on a spatial distribution of the amount of radiation received by the x-ray detector.

2. The metrology tool of claim 1, wherein the first amount of x-ray radiation includes one or more emission lines greater than 2,000 electron volts.

3. The metrology tool of claim 1, wherein the third amount of x-ray radiation includes one or more emission lines less than 1,840 electron volts.

4. The metrology tool of claim 1, wherein the secondary target includes any of Aluminum, Beryllium, and Carbon.

5. The metrology tool of claim 1, wherein the x-ray illumination optics subsystem is configured to shape and direct the first amount of x-ray radiation and the third amount of x-ray radiation to the specimen over a first inspection area of the specimen.

6. The metrology tool of claim 1, wherein the x-ray illumination optics subsystem includes a first x-ray illumination optics subsystem configured to shape and direct the first amount of x-ray radiation to the specimen over a first inspection area of the specimen and a second x-ray illumination optics subsystem configured to shape and direct the third amount of x-ray radiation to the specimen over a second inspection area of the specimen.

7. The metrology tool of claim 1, further comprising:
a wafer positioning system configured to selectively position the specimen at a plurality of different orientations about one or more axes of rotation parallel to a planar surface of the specimen, wherein the wafer positioning system is configured to selectively position the specimen within a range of at least one degree about the one or more axes of rotation.

8. The metrology tool of claim 1, further comprising:
an analysis engine configured to:
receive the signals generated by the x-ray detector to obtain a XRF measurement data set;
receive the signals generated by the photoelectron detector to obtain a XPS measurement data set;
determine at least one specimen parameter value based on a fitting analysis on the XRF measurement data set with an XRF response model and a fitting analysis of the XPS measurement data set with the XPS response model; and
store the at least one specimen parameter value.

9. The metrology tool of claim 8, wherein a value of the at least one specimen parameter is determined based on the fitting analysis on the XRF measurement data set and the determined value of the at least one specimen parameter is treated as a constant in the fitting analysis of the XPS measurement data set.

10. The metrology tool of claim 8, wherein the at least one specimen parameter is treated as a global parameter in a parallel fitting analysis including both the fitting analysis on the XRF data set and the fitting analysis of the XPS data set.

11. The metrology tool of claim 1, wherein the at least one x-ray illumination source and the x-ray detector are disposed in a confocal XRF measurement configuration or a total reflection XRF configuration.

12. A method comprising:
illuminating a specimen with a first amount of x-ray radiation generated by a primary target of an x-ray illumination source;
receiving an amount of radiation fluoresced from the specimen in response to the first amount of x-ray radiation;
generating signals indicative of a first property of the specimen in response to the amount of fluoresced radiation;
illuminating a secondary fluorescence target with a second amount of x-ray radiation generated by the primary target of the x-ray illumination source, wherein the secondary fluorescence target absorbs the second amount of x-ray radiation and emits a third amount of x-ray radiation in response to the absorbed amount or x-ray radiation, the third amount of x-ray radiation having a lower energy than the second amount of x-ray radiation;
illuminating the specimen with the third amount of x-ray radiation emitted by the secondary fluorescence target;
receiving an amount of photoelectrons emitted from the specimen in response to the third amount of x-ray radiation;
generating signals indicative of a second property of the specimen in response to the amount of photoelectrons;
repositioning at least a portion of the first and third amounts of incident x-ray radiation on the specimen based on the received amount of radiation fluoresced from the specimen and the received amount of photoelectrons emitted from the specimen, respectively; and
storing an indication of the signals indicative of the first and second properties of the specimen.

13. The method of claim 12, further comprising:
rotating the specimen to a plurality of different orientations out of plane from the surface of the specimen.

14. The method of claim 12, further comprising:
receiving the signals indicative of the first property of the specimen in response to the amount of fluoresced radiation to obtain a XRF measurement data set;
receiving the signals indicative of the second property of the specimen in response to the amount of photoelectrons emitted from the specimen to obtain a XPS measurement data set;
determining at least one specimen parameter value based on a fitting analysis on the XRF measurement data set with a XRF response model and a fitting analysis of the XPS measurement data set with the XPS response model; and
storing the at least one specimen parameter value.

15. The method of claim 14, wherein the determining the at least one specimen parameter values involves a combined analysis of the XRF and XPS measurement data sets by any of a feedback, feed forward, or multiple tool and structure analysis.

16. A non-transitory, computer-readable medium storing instructions that when executed by a computing system cause the computing system to:
control the illumination of a specimen with a first amount of x-ray radiation generated by a primary target of x-ray illumination source;
receive signals indicative of a first property of the specimen in response to an amount of radiation fluoresced from the specimen in response to the first amount of x-ray radiation;
control the illumination of the specimen with a second amount of x-ray radiation emitted by a secondary fluorescence target, wherein the second amount of x-ray radiation is emitted by the secondary fluorescence target in response to a third amount of x-ray radiation received from the primary target of the at least on x-ray illumination source and absorbed by the secondary fluorescence target, the second amount of x-ray radiation having a lower energy than the third amount of x-ray radiation;
receive signals indicative of a second property of the specimen in response to an amount of photoelectrons emitted from the specimen in response to the second amount of x-ray radiation;
reposition at least a portion of the first and second amounts of incident x-ray radiation on the specimen based on the received amount of radiation fluoresced from the specimen and the received amount of photoelectrons emitted from the specimen, respectively; and store an indication of the signals indicative of the first and second properties of the specimen.

17. The non-transitory, computer-readable medium of claim 16, wherein the first amount of x-ray radiation includes one or more emission lines greater than 2,000 electron volts.

18. The non-transitory, computer-readable medium of claim 16, wherein the second amount of x-ray radiation includes one or more emission lines less than 1,840 electron volts.

* * * * *